United States Patent

Shimamura et al.

[11] Patent Number: 5,876,717
[45] Date of Patent: Mar. 2, 1999

[54] POLYPEPTIDES CAPABLE OF BINDING TO HEAVY CHAINS OF IL-2 RECEPTORS

[75] Inventors: Toshiro Shimamura; Shinsuke Taki; Junji Hamuro, all of Kawasaki, Japan

[73] Assignee: Ajinomoto Co., Inc., Tokyo, Japan

[21] Appl. No.: 956,399

[22] Filed: Oct. 5, 1992

[30] Foreign Application Priority Data

Oct. 3, 1991 [JP] Japan ................................ 3-256335

[51] Int. Cl.[6] ........................ A61K 39/395; C07K 16/28; C12N 5/10; C12N 15/13
[52] U.S. Cl. .................... 424/154.1; 424/133.1; 424/135.1; 424/144.1; 424/152.1; 424/173.1; 530/387.3; 530/388.22; 530/388.7; 530/388.73; 530/388.75; 530/389.6; 536/23.4; 536/235; 536/23.53; 435/69.6; 435/69.7; 435/455; 435/471; 435/343.1; 435/343.2; 435/287.3; 435/310.1
[58] Field of Search ................................ 530/350, 388.22, 530/387.1, 387.3; 536/23.4, 23.5; 514/2, 12; 424/85.8, 141.1, 153.1, 130.1, 143.1, 154.1, 144.1, 173.1; 435/69.1, 240.2, 252.3, 252.33, 320.1, 325, 326

[56] References Cited

FOREIGN PATENT DOCUMENTS

| | | |
|---|---|---|
| 0 386 304 | 9/1990 | European Pat. Off. . |
| 0 395 853 | 11/1990 | European Pat. Off. . |
| 296 964 | 12/1991 | Germany . |
| 40 28 955 | 3/1992 | Germany . |
| WO 88/09344 | 12/1988 | WIPO . |
| WO 90/07861 | 7/1990 | WIPO . |

OTHER PUBLICATIONS

Shin et al (1989) Meth. Enzymol. 178, 459–476.

Ohbo et al (1991) J. Immunol. Meth. 142, 61–72.

Takeshita et al (1989) J. Exp. Med. 169, 1323–1332.

*Primary Examiner*—Christina Chan
*Assistant Examiner*—Phillip Gambel
*Attorney, Agent, or Firm*—Oblon, Spivak, McClelland, Maier & Neustadt, P.C.

[57] ABSTRACT

The present invention relates to (1) polypeptide capable of binding to β chain of IL-2 receptor and having the inhibitory activity of the binding between IL-2 and β chain of IL-2 receptor, and (2) the process of producing the polypeptide, especially in *E. coli* as a host. THe polypeptide according to the present invention and the pharmaceutical composition containing the polypeptide are useful to prevent rejection of organ transplantation and also to cure autoimmune diseases.

14 Claims, No Drawings

POLYPEPTIDES CAPABLE OF BINDING TO HEAVY CHAINS OF IL-2 RECEPTORS

BACKGROUND OF THE INVENTION

1. Field of the Invention

The present invention relates to novel polypeptides capable of binding to the heavy chains (also refered to as β-chains) of the human IL-2 receptor, thereby preventing human IL-2 from binding to the heavy chains of the human IL-2 receptor. The polypeptides according to the present invention can be included in a pharmaceutical compositions and are useful in immunomodulation for e.g. preventing graft rejection or curing autoimmune diseases, or leukemia, and thus they may be used as immunosuppressive agents.

2. Discussion of the Background

Due to the surprising improvement in surgical treatment for organ transplantation, the key to success therein has now been narrowed down to whether the graft rejection after the treatment can be inhibited. Graft rejection is caused when the body recognizes the graft as an extraneous material, and a series of immune responses are elicited to exclude it. Therefore, medicines such as so-called immunosuppresive agents including steroids, azathioprine, methonium compounds, 6-mercaptopurine, etc. have hitherto been administered as graft rejection inhibiting drugs. No significant increase in graft survival rate, however, has been observed because of their narrow safety margins and low effects, etc. Nevertheless with recently developed cyclosporin A the survival rate was drastically improved. Notwithstanding this, the drug was thereafter found to be severely nephrotoxic, and now its use is largely limited.

Accordingly, it has been desired that a less toxic and more effective immunosuppresive agent be developed.

IL-2 is a protein produced by helper T-cells, and has a wide variety of in vivo functions including growth and differentiation induction of killer T-cells and differentiation induction of B cells, thus being a very important factor of defence mechanisms. In organ- and bone marrow transplantation killer T cells, which have been activated by IL-2 or the like, have been shown to play an important role in host versus graft reaction (HVG reaction) or graft versus host reaction (GVH reaction) which is considered to hold the key to successful graft survival.

On the other hand, the immune system of the body is believed to attack the body itself if the system is disturbed, thereby causing autoimmune diseases, the causes for which most likely involve excessive production of IL-2 and other immunological factors or the overresponse thereto.

These facts suggest that selective and effective inhibition of response to IL-2 will lead to prevention of organ transplantation rejection and a cure for autoimmune diseases. In fact, it has been reported that IL-2, which is linked with a cellular toxin capable of selectively injuring IL-2 responsive cells with a receptor for IL-2 (hereunder abbreviated as IL-2 receptor), delayed the onset of and relieved arthritis when it was given to a rat suffering from adjuvant arthritis, an animal model for autoimmune diseases, and further that the immunological rejection by a mouse to the heart transplanted from another mouse of the same species was suppressed with the IL-2 compound administered upon the transplantation (Proc. Natl. Acad. Sci. USA, 86, 1008, 1989).

The IL-2/cellular toxin compound, however, has a short half-life in the blood, and thus its dose must be increased in order to be satisfactorily efficacious, thereby presenting the problem of side effects because of its large dose. In view of these facts, a less toxic medicine has been sought which adequately inhibits the response to IL-2.

The IL-2 receptor on IL-2 responsive cells is known to be composed of two glycoprotein molecules both capable of binding to IL-2 and comprising a β chain having a molecular weight of about 70.000 D and an α chain whose molecular weight is about 55.000 D.

It has been revealed, that the dissociation constant of the complex between IL-2 and the α chain is $10^{-8}$M and for the β chain $10^{-9}$M respectively, whereas the value decreases to as low as $10^{-12}$M if both, the α and the β chains simultaneously bind IL-2 to form a strongly joined three membered associate. Cells with only the α chain present thereon do not respond to IL-2 bound thereto, but cells with both the α and β chains present thereon cause various biological activities due to the binding of IL-2. Therefore it is now understood, that the presence of the β chain in the IL-2 receptor is indispensable to the performance of physiological activities of IL-2. That is, it is assumed, that the response to IL-2 will be inhibited by blocking the binding between IL-2 and the β chain.

However, at present there are no substances known, which specifically inhibit the linking between IL-2 and the β chains of IL-2 receptors, with the exception of an anti-IL-2 receptor chain antibody (refer to Japanese Patent Application Disclosure No. HEI 2-18527). Nevertheless this single known antibody is a foreign protein obtained by immunizing xenogenic rabbits and mice. Thus, when the antibody is administered to a human in the form obtained, an immune response occurs against it causing serious side effects such as anaphylactic shock and serum diseases. It is surmised, that the effect of the antibody is weakened, which unfortunately complicates its immediate use in clinical situations.

In order to overcome the drawbacks of these antibodies prepared from xenogenic animals in clinical applications, genetic engineering techniques were developed to convert the constant region (also called C region) of an antibody, which plays no direct part in binding to the antigen to the C region of a human antibody (Methods in Enzymology 178, 459, 1989), heightening hopes for clinically applicable antibodies.

Generally, when an antibody is clinically used, the expected effects of said antibody may be divided into two large categories. The first type of effect is where an antibody combines with an antigen to form an immune complex, and the complement or immune cells are mobilized to eliminate the antigen. This is true for cell surface antigens, etc., in which case the c region of the antibody is indispensable for stimulation of the complement system, and an antibody whose C region is converted to a human type would be effective. The other effect is where the antigen activity is suppressed due to binding of the antibody to the antigen. This includes the case, where the antigen is a bioactive substance or its receptor, or an enzyme, in which case the C region of the antibody is unnecessary. On the contrary the absence of the C region is most desirable, since by administration of the antibody into the body an immune complex thereof with an antigen is formed. In this case, if the antigen is a cell then the cell may be destroyed, and if the antigen is a soluble antigen then it may be trapped in the kidneys causing inflammation. In addition, the molecular weight of the complete antibody containing both the variable regions (also called V region) and the C regions is 150–900 KD compared to a molecular weight of as small as 27 KD for an antibody composed of only the V regions, for which reason the latter is more easily administered to the body.

In order to produce only the V regions of an antibody from antibody protein, it is necessary to obtain a heavy chain (hereunder called H chain) of the antibody and a light chain (hereunder called L chain) of the V region through protease digestion, and induce the binding between them through an appropriate method in order to produce a functional antibody V region molecule. However, it is impossible with present techniques to produce a functional antibody V region molecule with high efficiency and ease.

SUMMARY OF THE INVENTION

It is, therefore, an object of the present invention to provide a polypeptide containing a functional antibody V region molecule capable of binding specifically to the β chain of human IL-2 receptor and selectively inhibiting the binding between said chain of the human IL-2 receptor and IL-2; a DNA sequence which codes for said polypeptide; a recombinant vector containing said DNA sequence and being capable of expressing said DNA sequence; a transformant containing said recombinant vector; a method for producing the desired polypeptide by culturing said transformant, a pharmaceutical composition comprising said polypeptide. This polypeptide promises to be usable as an effective immunomodulating and immunosuppressive agent, for e.g. preventing the rejection of a graft and for the treatment of inflammatory diseases such as allergic diseases and autoimmune diesases, and for the treatment of leukemia and the like.

DETAILED DESCRIPTION OF THE PREFERRED EMBODIMENTS

As a result of diligent research by the present inventors in order to achieve a solution of the above problems the method of production described below was devised for a polypeptide containing a functional antibody V region molecule capable of selectively inhibiting the binding between the target β chain of human IL-2 receptor and IL-2, thus completing the present invention.

That is, the present invention relates to a method of producing a polypeptide capable of (1) binding to the β chain of a human IL-2 receptor and (2) selectively inhibiting the binding between IL-2 and said β chain of the human IL-2 receptor; a DNA sequence which codes for said polypeptide; an recombinant expression vector comprising said DNA sequence and being capable of expressing said polypeptide; a transformant containing said recombinant expression vector; a process for producing the object polypeptide by culturing said transformant; a pharmaceutical composition comprising said polypeptide; and an immunomodulating agent such as an immunosuppressive agent, which includes said polypeptide.

The polypeptide according to the present invention is capable of binding to the β chain of the human IL-2 receptor and selectively inhibits the binding between said β chain of the human IL-2 receptor and IL-2, and is thus useful in immunomodulation, particularly immunosuppression such as e.g. preventing graft rejection and the like.

The preferred polypeptide according to the present invention may be shown by the sequence (I) (SEQ ID NO:2)

| Met | Asp | Ile | Leu | Leu | Thr | Gln | Ser | Pro | Ala | Ile | Leu | Ser | Val | Ser | Pro |
| Gly | Glu | Arg | Val | Ser | Phe | Ser | Cys | Arg | Ala | Ser | Gln | Ser | Ile | Gly | Thr |
| Ser | Ile | His | Trp | Tyr | Gln | Gln | Arg | Thr | Asn | Gly | Ser | Pro | Arg | Leu | Leu |
| Ile | Lys | Tyr | Ala | Ser | Glu | Ser | Leu | Ser | Gly | Ile | Pro | Ser | Arg | Phe | Ser |
| Gly | Ser | Gly | Ser | Gly | Thr | Asp | Phe | Thr | Leu | Ser | Ile | Thr | Ser | Val | Asp |
| Ser | Glu | Asp | Ile | Ala | Asp | Tyr | Tyr | Cys | Gln | Gln | Thr | Asn | Ser | Trp | Pro |
| Thr | Thr | Phe | Gly | Gly | Gly | Thr | Lys | Leu | Glu | Leu | Lys | Val | Asp | Lys | Ser |
| Ser | Gly | Ser | Gly | Ser | Glu | Ser | Lys | Ser | Thr | Gln | Val | Lys | Leu | Glu | Glu |
| Ser | Gly | Pro | Gly | Leu | Val | Lys | Pro | Ser | Gln | Ser | Leu | Ser | Leu | Thr | Cys |
| Thr | Val | Thr | Gly | Tyr | Pro | Ile | Thr | Ser | Asp | Tyr | Ala | Trp | Asp | Trp | Ile |
| Arg | Gln | Phe | Pro | Gly | Asn | Lys | Leu | Glu | Trp | Met | Gly | Tyr | Val | Ser | Tyr |
| Ser | Gly | Ser | Thr | Asp | Tyr | Asn | Pro | Ser | Leu | Lys | Ser | Arg | Ile | Ser | Ile |
| Ser | Arg | Asp | Thr | Ser | Lys | Asn | Gln | Phe | Phe | Leu | Gln | Leu | Asn | Ser | Val |
| Thr | Thr | Glu | Asp | Thr | Ala | Thr | Tyr | Tyr | Cys | Ala | Arg | Gly | Gly | Phe | Pro |
| Tyr | Ala | Met | Asp | Tyr | Trp | Gly | Gln | Gly | Thr | Thr | Val | Thr | Val | Ser | Ser | or the sequence (II) (SEQ ID NO:4)

| Met | Asp | Ile | Gln | Leu | Thr | Gln | Ser | Pro | Ala | Ile | Leu | Ser | Val | Ser | Pro |
| Gly | Glu | Arg | Val | Ser | Phe | Ser | Cys | Arg | Ala | Ser | Gln | Thr | Ile | Gly | Thr |
| Ser | Ile | His | Trp | Tyr | Gln | Gln | Arg | Thr | Asn | Gly | Ser | Pro | Arg | Leu | Leu |

-continued

| | | | | | | | | | | | | | |
|---|---|---|---|---|---|---|---|---|---|---|---|---|---|
| Ile | Lys | Tyr | Ala | Ser | Glu | Ser | Ile | Ser | Gly | Ile | Pro | Ser | Arg | Phe | Ser |
| Gly | Ser | Gly | Ser | Gly | Thr | Asp | Phe | Thr | Leu | Ser | Ile | Asn | Asn | Val | Glu |
| Ser | Glu | Asp | Ile | Ala | Asp | Tyr | Tyr | Cys | Gln | Gln | Thr | Asn | Thr | Trp | Pro |
| Thr | Thr | Phe | Gly | Ser | Gly | Thr | Lys | Leu | Glu | Leu | Lys | Val | Asp | Lys | Ser |
| Ser | Gly | Ser | Gly | Ser | Glu | Ser | Lys | Ser | Thr | Gln | Val | Lys | Leu | Glu | Gln |
| Ser | Gly | Gly | Gly | Leu | Val | Lys | Pro | Gly | Gly | Ser | Leu | Lys | Leu | Ser | Cys |
| Ala | Ala | Ser | Gly | Phe | Ala | Phe | Ser | Ser | Tyr | Asp | Met | Ser | Trp | Val | Arg |
| Gln | Thr | Pro | Glu | Lys | Arg | Leu | Lys | Trp | Val | Ala | Thr | Phe | Ser | Ser | Asp |
| Gly | Ser | Asp | Thr | Asp | Tyr | Pro | Asp | Ser | Val | Lys | Gly | Arg | Phe | Thr | Ile |
| Ser | Arg | Asp | Asn | Ala | Arg | Asn | Thr | Leu | Tyr | Leu | Gln | Met | Ser | Ser | Leu |
| Arg | Ser | Glu | Asp | Thr | Ala | Leu | Tyr | Tyr | Cys | Ala | Arg | Gly | Tyr | Pro | Tyr |
| Ala | Met | Asp | Tyr | Trp | Gly | Gln | Gly | Thr | Thr | Val | Thr | Val | Ser | Ser | | without being limited thereto.

It may be anyone capable of binding to the β chain of a human IL-2 receptor. This includes polypeptides, which are selected from the following group: (a) polypeptides which in respect to sequences (I) or (II) are deficient in one or more amino acids; (b) polypeptides which with respect to sequences (I) or (II) lack the N-terminal Met residue; (c) polypeptides which in respect to (I) or (II) and/or (a) and/or (b) have additively connected thereto one or more aminoacids, whereby the additively connected aminoacids do not interfere with the biological activity and/or may be easily eliminated. In addition the polypeptides according to the invention can also be acetylized, amidized or may contain polyethylen etc. added thereto, as long as they bind to the human IL-2 receptor β chain and selectively inhibit binding between the human IL-2 receptor β chain and IL-2.

Particularly, in some cases the Met residue of each terminal of the polypeptides (I) or (II) is cut off during expression or the purification process, resulting in the N-terminal becoming Asp. The thus modified polypeptides have the characteristics mentioned above, i.e. they are capable of binding to the heavy chain of human IL-2 receptor and inhibit the binding between IL-2 and the heavy chain of IL-2 receptor. They are further capable of the above even when the Met of each N-terminal has been removed with an enzyme such as aminopeptidase, after production of the polypeptides containing Met.

In addition, when the need arises a polypeptide according to the present invention may be used in combinations with toxins.

The polypeptides of the present in invention may be coded by DNA sequence (III) (SEQ ID NO:1)

```
ATG GAT ATT CTG CTG ACC CAG TCT CCA GCC ATC CTG TCT GTG AGT CCG  48
GGA GAA AGA GTC AGT TTC TCC TGC AGG GCC AGT CAG AGC ATT GGC ACA  96
AGC ATA CAC TGG TAT CAG CAA AGA ACA AAT GGT TCT CCA AGG CTT CTC  144
ATT AAA TAT GCT TCT GAG TCT CTC TCT GGG ATC CCT TCC AGG TTT AGT  192
GGC AGT GGA TCA GGG ACA GAT TTT ACT CTT AGC ATC ACC AGT GTG GAT  240
TCT GAA GAT ATT GCA GAT TAT TAC TGT CAA CAA ACT AAT AGC TGG CCA  288
ACG ACG TTC GGT GGA GGG ACC AAG CTG GAG CTC AAA GTC GAC AAA TCC  336
TCA GGA TCT GGC TCC GAA TCC AAA AGC ACG CAG GTC AAA CTC GAG GAG  384
TCT GGA CCT GGC CTG GTG AAA CCT TCT CAG TCT CTG TCC CTC ACC TGC  432
ACT GTC ACT GGC TAC CCA ATC ACC AGT GAT TAT GCC TGG GAC TGG ATC  480
CGG CAG TTT CCA GGA AAC AAA CTG GAG TGG ATG GGC TAC GTA AGC TAC  528
AGT GGT AGC ACT GAC TAC AAC CCA TCT CTC AAA AGT CGA ATC TCT ATC  576
AGT CGA GAC ACA TCC AAG AAC CAG TTC TTC CTG CAG TTG AAT TCT GTG  624
ACT ACT GAG GAC ACA GCC ACA TAT TAC TGT GCA AGA GGT GGT TTC CCC  672
TAT GCT ATG GAC TAC TGG GGT CAA GGG ACC ACG GTC ACC GTC TCC TCA  720
``` or DNA sequence IV (SEQ ID NO:3)

```
ATG GAC ATT CAG CTG ACC CAG TCT CCA GCC ATC CTG TCT GTG AGT CCA   48

GGA GAA AGA GTC AGT TTC TCC TGC AGG GCC AGT CAG ACC ATT GGC ACA   96

AGC ATA CAG TGG TAT CAG CAA AGA ACA AAT GGT TCT CCA AGG CTT CTC  144

ATA AAG TAT GCT TCT GAG TCT ATC TCT GGG ATC CCT TCC AGG TTT AGT  192

GGC AGT GGA TCA GGG ACA GAT TTT ACT CTT AGC ATC AAG AAT GTG GAG  240

TCT GAA GAT ATT GCA GAT TAT TAC TGT CAA CAA ACT AAT ACC TGG CCA  288

ACG ACG TTC GGC TCG GGG ACC AAG CTG GAG CTC AAA GTC GAC AAA TCC  336

TCA GGA TCT GGC TCC GAA TCC AAA AGC ACG CAG CTC AAA CTC GAG CAG  384

TCA GGG GGA GGC TTA GTG AAG CCT GGA GGG TCC CTG AAA CTC TCC TGT  432

GCA GCC TCT GGA TTC GCT TTC AGT AGT TAT GAC ATG TCT TGG GTT CGC  480

CAG ACT CCG GAG AAG AGG CTG AAG TGG GTC GCA ACC TTT AGT AGT GAT  528

GGT AGT GAC ACC GAC TAT CCA GAC AGT GTG AAG GGC CGA TTC ACC ATC  576

TCC AGA GAC AAT GCC AGG AAC ACC CTG TAC CTG CAA ATG AGC AGT CTG  624

AGG TCT GAG GAC ACG GCC TTG TAT TAC TGT GCA AGG GGG TAC CCC TAT  672

GCT ATG GAC TAC TGG GGT CAA GGG ACC ACG GTC ACC GTC TCC TCA      717
```

Also DNA sequences, which hybridize to said DNA sequences (III) and/or (IV) are subject matter of the present invention.

According to the present invention, a polypeptide is provided which contains a functional antibody V region molecule which selectively inhibits the binding between the β chain of human IL-2 receptor and IL-2.

The present inventors first prepared a hybridoma clone capable of producing a mouse monoclonal antibody which is specific to the β chain of human IL-2 receptor and which inhibits the binding of IL-2 to the human IL-2 receptor.

The method of preparing the hybridoma clone capable of producing the monoclonal antibody to the human IL-2 receptor β chain is described below.

A hybridoma is produced by fusion of a myeloma cell and an antibody producing cell. As the antibody producing cell, a spleen or lymph node cell may be used from a mouse or rat which has been immunized with TL-Mor cells which are human T-cell leukemia virus infected T cells expressing a high number of β chain molecules of IL-2 receptor. As the cell for immunization, any cell may be used, which is a human cell expressing β chain molecules of IL-2 receptors, other than TL-Mor cells. Further the β chain molecules themselves purified from those cells may be used without any problems.

The antibody producing cell and the myeloma cell may be taken from different animals as long as they can be fused together, but better results are generally obtained with cells from the same animal. One hybridoma whose use is preferred in the present invention is the one between a spleen cell or lymph node cell and a myeloma cell of a mouse which has been immunized with TL-Mor cells, a T cell line, infected with a human T cell leukemia virus.

For example, excellent results described in the following example were obtained using the hybridoma between a spleen cell and a myeloma cell SP2/0-Ag14 of a Balb/c mouse which had been immunized with TL-Mor cells suspended in physiological saline.

The myeloma cell may be, in addition to SP2/0-Ag14, any 8 azaguanine resistant cell strain such as X63-Ag8-6.5.3, P3-X63-Ag8-U1, P3-X63-Ag8, P3-NSI/1-Ag4-1, MPC11-4.5.6.TG.1.7 (mouse cells); 210.RCY.Ag1.2.3 (rat cells); and SK0-007,GH15006TG-A12 (human cells). Preparation of hybridomas and selection of the clones among them which produce monoclonal antibodies capable of binding to the β chain of human IL-2 receptor to inhibit the biological activity of IL-2 can be done, for example, in the following manner. Fusion of the antibody producing cell and the myeloma cell is done using polyethylene glycol or Sendai virus. Only the fused hybridomas may be grown in a culture (HAT culture medium) which includes hypoxanthine, thymidine and aminopterin. Not all of the obtained hybridomas produce antibodies, however, nor do all of the antibody producing hybridomas produce the target antibody. Therefore, it is necessary to select out of the hybridoma clones those clones which produce monoclonal antibodies capable of binding to the β chain of human IL-2 receptor to inhibit the biological activity of IL-2.

This selection may be done in the following manner. That is, the primary screening involves preparation of $^{125}$I labelled human IL-2 and measurement of the degree of inhibition of binding of the $^{125}$I labelled human IL-2 to TL-Mor cells, which express the β chain molecules and α chain molecules of a human IL-2 receptor using the supernatant of the hybridoma culture. The secondary screening involves measuring the degree of inhibition of binding of $^{125}$I labeled human IL-2 using the supernatnant of the hybridoma culture to MT-1 cells which are human adult T cell leukemia virus infected T cells expressing only the α chain of human IL-2 receptor. If the supernatant of the hybridoma culture inhibits the binding of IL-2 to TL-Mor cells, but does not inhibit the binding between MT-1 cells and IL-2, the the hybridoma is a producer of an antibody against the β chain molecules of the IL-2 receptor.

The method of producing a $^{125}$I labelled human IL-2 may be one such as the Bolton-Hunter method, the lactoperoxidase method or the chloramin T method, as long as the biological activity of IL-2 is maintained. Also the cells to be used in the primary screening may be any cells which are human cells expressing both β and α chains. Further, the cells to be used in the secondary screening may be any cells which are human cells expressing either the β chain or the α chain.

The total RNA is extracted from the thus obtained hybridoma clone, and the gene (cDNA) which codes for the V regions of the monoclonal antibody is collected. The present inventors diligently sought a method of obtaining cDNA at a greater speed, and thus the cDNAs which code for the V regions were obtained according to the method described below.

That is, a DNA sequence, 20 to 30 nucleotides in length (primer DNA), with a high compatibility with the 5' and 3' termini of the mRNA sequence for each of the V regions were considered, based on the nucleotide sequence of the H and L chains of mouse IgG, whose nucleotide sequence is already known.

Then the 5' end primer is designed in the direction from the 5' end to the 3' end, and the ATG sequence which is the translation initiation code is attached to the 5' end of the primer for the V regions of the L chain. For the 3' end primer, the translation termination code is attached to the primer for the H chain at the 3' end thereof. In the case of the 3' end primer, the complementary sequence need only be redesigned in the direction from the 3' end to the 5' end.

Obviously, the ATG sequence may be alternatively attached to the 5' end of the primer for the V region of the H chain, and the termination codon attached to the 3' end of the primer for the V region of the L chain. TAA, TAG or TGA may be used as the termination codon, but TGA was used as the termination codon in the example of the present invention.

Next, an appropriate restriction enzyme site is introduced at the 5' end (for the 3' end primer, the 5' end after redesigning) of each primer DNA for the H and L chains in order to allow the insertion in an expression vector. The designed primer DNA is chemically synthesized using a DNA synthesizer.

Next, the total RNA is extracted from the obtained hybridoma according to a well-known method, and a single stranded cDNA is produced using a reverse transcriptase and the 3' end primer DNA. The DNA fragments which code for the V regions of the H and L chains of the antibody are each selectively amplified and obtained according to the Polymerase Chain Reaction method with Taq polymerase (PCR method, Science, 230, 1350, 1985), using the 5' end primer DNA and the 3' end primer DNA.

When the cDNAs which code for these V regions are expressed in E. coli and functional antibody V regions molecules are prepared, each of the cDNAs may be expressed separately or may be incorporated into one vector simultaneously and the expressed ones may be assembled; however, the efficiency of this method is known to be extremely low (Science, 240, 1038, 1988).

Originally an antibody is a dimer wherein an H chain and an L chain are covalently bonded by an SS crosslink and the H chains are further bonded together with an SS linkage. The SS crosslinks between the H chain and the L chain are located in the C regions, and the V regions are non-covalently bonded together.

Therefore, when preparing antibody V region molecules it is necessary to rely solely on these non-covalent bonds, which may be a reason for the low efficiency of formation of the functional molecules. Recently, each of the V regions are linked using a linker peptide, and a technique has been developed for expressing a single chain functional molecule with E.coli (Science, 242, 423, 1988). The present inventors applied this technique to successfully express a polypeptide including the V regions of a functional single stranded anti-IL-2 receptor β chain antibody composed only of the V regions of the antibody.

In other words, an expression vector is first constructed which contains, in the following order, an upstream promoter region; a ribosome binding region; a restriction enzyme site introduced into a 5' end primer having an ATG sequence attached thereto; a restriction enzyme site introduced into a 3' end primer for the same chain; a DNA sequence coding for the linker peptide of a length necessary to connect the V region of the L chain of the antibody with the V region of the H chain of the antibody; and a restriction enzyme site introduced into a 5' end primer having no ATG sequence; a restriction enzyme site introduced into a 3' end primer for the same chain; and a final terminator region.

At this time, when each V region DNA which was amplified according to the PCR method is introduced, care must be taken, that there is no slipping in the reading frame of the linker peptide or the subsequent V region DNA.

The origin of the promotor in the present invention is not important and use may be made, without being limited thereto of for example trp promotor, tac promotor, trc promotor or lac promotor of E. coli, or λPL promotor or λPR promotor of λ phage, in case the polypeptide is to be expressed in a prokaryote such as E.coli, or the SV40 promotor, ADHI promotor of yeast or the like in case expression is to be carried out in an eucaryote. The ribosome binding region may be, without being limited thereto for example a ribosome binding region of trpL, ropE or LacZ from E.coli, or a ribosome binding region of trpL, ropE or lacZ from E.coli, or a ribosome binding region of the CII protein from λ phage, or a ribosome binding region of SV40 t-Antigen or the like. A chemically synthesized DNA sequence, which may be adapted to the host, i.e. eucaryote or procaryote, may also be used. In addition two or more ribosome binding regions may be used for e.g. larger accumulation of the target polypeptide as inclusion bodies within E.coli.

The sequences of the linker polypeptides connecting each of the antibody V regions may be any ones with which the prepared antibody V region molecules are functional, but it is preferable to use a sequence which will minimize the side effects when administered to the body, and which does not have a unique secondary structure.

The terminator may be for example trp terminator, rrnB terminator or recA terminator from E.coli or any terminator usable in expression in eucaryotes such as for example yeast. It is also generally preferable, that the number of copies of the expression vector be as large as possible. In E.coli it is prefered that the replication start point is that from pUC vector. V region DNAs of the H and L chains which are amplified according to the PCR method are inserted in the expression vector.

After insertion, the expression vector may be inserted into a host by a conventional transformation method, and then expressed. The organisms for causing expression may be either a procaryote or eucaryote. Examples of procaryotic organisms which may be used include E. coli, Bacillus subtilis, etc. The eucaryotic organism may be, for example, yeast, CHO cells, etc. It is preferable to use a procaryotic organism as the host, more preferably E. coli. Any conventional method may be used to incorporate the expression vector into these organisms. For example with E.coli, cells being in the logarithmic growth phase are treated with 50 mM of calcium chloride for 30 min on ice in order to modify the structure of the cell walls of E.coli, and this is followed by the addition of recombinant plasmid DNA to cells. About 10 minutes thereafter heat is applied at 30° C. to 42° C. for 2 minutes. Following this, a culture medium is added and the mixture is cultured at 30° C.–37° C. for about one hour, allowing the expression of the vector DNA incorporated into the organism.

The objective polypeptide, which contains the functional antibody V regions can be accumulated in such an organism or culture medium by growing said organism therein. The culture medium may be any well known one which is capable of causing the growth of each of the organisms, and conventional culturing conditions are acceptable. After culturing, the desired functional antibody V region molecules may be obtained by any commonly known method. The polypeptide according to the present invention is capable of binding to the β chain of the human IL-2 receptor and selectively inhibits the binding between the β chain of human IL-2 receptor and IL-2.

An immunomodulating agent according to the present invention such as an immunosuppressant should contain o,1% to 100% by weight of the above mentioned polypeptide, preferably 0,5% to 70% by weight. Thus the polypeptide according to the present invention may be administered as is, or as a preparation obtained by mixing with a conventional carrier. Any carrier normally used in the preparation field is acceptable as long as it does not react with a polypeptide according to the present invention. An injection solution may be prepared by dissolving a polypeptide according to the present invention in water, but depending on the need it may be dissolved in physiological saline, or a glucose solution, in which a buffer, a preservative, a stabilizer or an excipient may be included. Also, these preparations may include any other ingredients which are deemed of value in treatment.

An immunosuppresive agent according to the present invention may be administered orally, by injection or intrarectally, but administration by injection is preferable. The dose depends upon the method of administering and the symptoms and age of the patient; however normally a dose of 0.001 to 1000 mg is given, and preferably 0.01 to 10 mg is administered 1–3 times per day.

A more detailed explanation will now be made based on examples of the present invention. However, the present invention is not limited to these examples.

EXAMPLES

Example 1

Preparation of Hybridomas

Six to eight week old male BALB/c mice were immunized by intraperitoneal injection of 1'10–7/mouse of TL-Mor cells suspended in physiological saline. Additional immunization was carried out in the same manner ten days later. Further 5 days thereafter blood was collected via the orbital vein of each mouse, and its antibody titer was measured on the basis of its activity of preventing $^{125}$I labelled IL-2 from binding to the TL-Mor cells in a manner described in the reference example given later. Those mice determined to have high antibody titers were subjected to final immunization in the same manner as the above, 3 days after which the spleens were extirpated. The spleen cells and mouse myeloma cells were mixed at a cell count ratio of 10:1 in the presence of 50% polyethylene glycol #4000 (manufactured by Nakara Tesague Inc.) for cell fusion.

The fused cells were suspended in a RPMI1640 culture medium (manufactured by Gibco Inc.) containing 10% fetal bovine serum (Gibco Inc.) to a concentration of 5×10$^6$ cells/ml. One hundred ml aliquots of the resulting suspension were poured into each well of a 96 welled flat bottom plate (manufactured by Corning Inc.) containing 5×10$^6$ mouse thymic cells in each well. Half of the medium was replaced by a separate medium containing hypoxanthine, aminopterine and thymidine (HAT culture medium) 1, 2, 3 and 6 days later. The same replacement was repeated every 3 days thereafter. About 2 weeks after the fusion a determination was made of the ability to prevent $^{125}$I-labelled Il-2 from binding to TL-Mor cells and to MT-1 cells using culture supernatant of each well after the growth of the fused cells (hybridomas). Only those hybridomas of the wells which proved to inhibit the binding to TL-Mor cells were cloned according to the limiting dilution culture method.

Measurement of the inhibiting ability of the culture supernatants of the respective hydridoma clones was led to the discovery of hybridomas which produce an anti-IL-2 receptor β chain antibody. Then the culture supernatants of the thus found hybridomas producing the anti-IL-2 receptor β chain antibody were tested their ability to suppress the biological activity of IL-2 in the manner described below. That is, an ILT-Mat cell solution prepared by suspending ILT-Mat cells into a RPMI1640 culture medium with 10% of fetal bovine serum to a concentration of 5×10$^6$ cells/ml. One hundred ml aliquots of the suspension were poured into each well of a 96 welled flat bottom plate, after which 50 μl of the the sample culture supernatant was added to each well and incubated at 37° C. for 30 minutes. Thereafter a solution containing 200 u/ml of human recombinant IL-2 was prepared with an PRMI1640 medium containing 10% fetal bovine serum, and the 50 μl aliquots thereof were added to the wells and cultured in the presence of 5% $CO_2$ at 37° C. for 48 hours. The culture during the final 4 hours was carried out in the presence of 1 μCi of $^3$H-thymidine (produced by Du Pont Inc.) added to each wells, and the radioactivity level taken in the cells was measured with a scintillation counter (manufactured by Packard Inc.) to determine wether the culture supernatants are capable of inhibiting the biological activity of IL-2. Thus those hybridomas, which produce an antibody to an anti-IL-2 receptor β chain were prepared. The prepared hybridomas include TU27 (Ferm BP-2510) and TU25 (FERM BP 3529).

Example 2

Preparation of cDNA for V Regions of the Antibody from the Hybridomas

Washing of 5×10$^6$ TU27 or TU25 bybridoma was done with PBS, after which a buffer solution for RNA extraction containing guanidine thiocyanate, N-lauryl sarcosine and EDTA was added thereto to prepare a suspension which was then laid on an equivolume of a cesium chloride solution previously placed in a tube. The mixture was subjected to centrifugation at 125,000 G for 16 hours. The supernatant was collected by suction, and to 10 mM of a Tris/HCl buffer solution (pH 7.5) conatining 1 mM of EDTA was added to prepare suspension which was then placed in a separate tube and incubated at 65° C. for 5 minutes. To the mixture one tenth volume of 2M of potassium acetate (pH 5.0) (produced by Pharmacia Inc.) and three fold volume of ethanol (produced by Nakaraitesgue Inc.) were added, and the resulting solution was allowed to stand at −20° C. overnight. The solution was then subjected to centrifugation at 5,000×g for 20 minutes followed by removal of the supernatant. The residue was treated by centrifugal washing with 80% ethanol, and then dried. It was dissolved in a 10 mM Tris HCl buffer solution (pH 7.5) containing 1 mM of EDTA to provide a total RNA fraction.

Next a solution of a primer, which was previously designed to be complementary to the 3' end of the V regions of the H and L chains of the antibody (final content: 1 μM), a mixture solution of deoxy NTP, a buffer solution for cDNA synthesis (produced by Amersham Inc.), a RNAse inhibitor (produced by Takara Shuzo Inc.) and a reverse transcriptase (produced by Takara Shuzo Inc.) was added to the total RNA fraction, followed by a one hour reaction at 42° C. for the synthesis of single stranded cDNAs to which a buffer solution for PCR (produced by Cetus Inc.), a mixture solution of deoxy NTP, 5' and 3' end primers as shown in FIG. 1, for amplification containing of the single stranded cDNA's for the V regions of the H and L chains of the antibody (the final content of each primer: 1 $\mu$M), and a Taq polymerase (produced by Takara Shuzo Inc.) was added, after which the PCR (Cetus Inc., thermal cycler) was carried out. The reaction cycle comprised denaturation for 30 seconds (94° C.), annealing for 30 seconds (55° C.) and polymerisation for 1 minute (72° C.) and it was repeated 30 cycles; the polymerisation time was increased by 15 seconds for each cycle.

After the reaction was completed, agarose gel electrophoresis was carried out with a 40 mM Tris acetate buffer solution containing 1 mM of EDTA, and the corresponding cDNA fragment was cut out. The extraction and purification thereof was carried out with a GENE CLEAN kit (manufactured by Bio 101 Inc.).

Example 3

Construction of Expression Vector

A larger DNA fragment prepared by cutting pT13SNco (E. coli AJ-12447 containing this plasmid is deposited under FERM P-10757) with restriction enzymes ClaI and BamHI (both produced by Takara Shuzo Inc.) was joined with a synthetic DNA fragment (linker) prepared in a conventional manner using a T4 DNA ligase (produced by Takara Shuzo Inc.).

Then, a synthetic DNA fragment was ligated with a larger fragment prepared by cutting plasmid pT13SNco with restriction enzymes ClaI and BamHI to prepare another plasmid which was in turn cut with restriction enzymes EcoRI and PvuII (both produced by Takara Shuzo Inc.). pUC18 (Messin J., "Methods in Enzymology", vol. 101, pp. 20–78, 1983) was cut with a restriction enzyme at its HindIII and NdeI sites, and then made blunt with T4 DNA Polymerase (produced by Takara Shuzo Inc.) and then ligated with T4 ligase and cut with EcoRI and HincII (produced by Takara Shuzo Inc.). The smaller one of the DNA fragments prepared as mentioned above by the cutting with enzymes EcoRI and PvuII was joined with the larger one of the DNA fragments prepared by the cutting with EcoRI and HincII using T4 ligase to provide pFv-DE having the replication initiation point of pUC.

Example 4

Introduction of a cDNA for Antibody V Regions into pFv-DE and Preparation of Antibody Producing Cells Consisting Only of the V Regions First pFv-DE was cut with restriction enzymes NdeI and SalI (Takara Shuzo Inc.). With T4 ligase the resulting larger DNA fragment was united with a fragment prepared by cutting the cDNA for the V regions of the L chains of TU25 and TU27 recovered after the PCR with the same enzymes NdeI and SalI. The V regions of the L chains of TU25 correspond to the 4th to the 324th bases of the base sequence listed under Sequence Identification No. 2 in the sequence table, while the V regions of the L chains of TU27, to the 4th to the 324th bases of the base sequence whose identification No. is 2 in the sequence table. The 1st to 3rd bases in each base sequence are the translation initiation codon ATG.

The united plasmid was then cut with restriction enzymes XhoI and HindIII (Takara Shuzo Inc.). With T4 ligase the resulting larger DNA fragment was ligated with a fragment prepared by cutting the cDNA for the V regions of the H chains of TU27 and TU25 recovered after the PCR with the same enzymes XhoI and HindIII thereby constructing pFv (TU27)-DE and pFv(TU25)-DE which express an antibody consisting only of the V regions. Thereafter the respective plasmids were transformed into E. coli HB101 strains to provide cells which produce an antibody consisting only of the V regions, E. coli pFv(TU27)-DE/HB101 AJ-12646 (FERM BP-3973) deposited on Sep. 7, 1991 and E.coli pFv(TU25)-DE/HB101 AJ-12647 (FERM BP-3974) deposited on Sep. 7, 1991. The address of the depository is National Institute of Bioscience and Human Technology, formerly the Fermentation Research Institute, Agency of Industrial Science and Technology, 1–3, Higashi 1 chome Tsukuba-shi Ibaraki-ken, 305, Japan. The V regions of the H chains of TU27 conform to the 367th to the 720th bases of the base sequence listed under sequence identification No. 1 in the sequence table, while the V regions of the H chains of TU25, to the 367th to the 717th bases of the base sequence whose identification No. is 2 in the sequence table.

Example 5

Production with Antibody Producing Cells with Only the V Regions

The resulting transformed strains E. coli pFv(TU27)-DE/HB101 FERM BP-3973) and E.coli pFv(TU25)-DE/HB101 (FERM BP-3974) were grown in 5 ml of 2×TY [1.6% trypton, 1% yeast extracts (both are produced by Bacto Inc.), 0.5% NaOH, pH 7.0] containing 50 $\mu$g/ml of ampicillin at 37° C. overnight. Then 5 ml of the resulting culture suspension was seeded into 100 ml of a M9-casamino acid culture medium (0.6% $Na_2HPO_4 \cdot 12H_2O$, 0.3% $KH_2PO_4$, 0.05% NaCl. 0.1% $NH_4Cl$, 0.05% $MgSO_4 \cdot 7H_2O$, 0.00147% $CaCl_2$, 0.2% glucose, 0.2% of casamino acid, 0.02% of L-leucine, 0.02% L-proline, 0.0002% thiamine HCl, 100 $\mu$g/ml of ampicillin, pH 6.9) followed by incubation at 37° C. for 3 hours. Then 3-indoleacrylic acid (IAA) was added to the culture to a concentration of 25 $\mu$g/ml, after which the induction incubation was continued at 37° C. for an additional 20 hours. Part of the resulting cell suspension was observed with a phase contrast microscope of about 1,500 magnification to find the presence of inclusion bodies in E.coli cells.

The thus cultivated cell suspension was then treated with a centrifuge to collect the cells. For the double concentration a 20 mM Tris HCl buffer solution containing 30 mM of NaCl (pH 7.5) was added to the culture to prepare a suspension. The resulting suspension was then treated with the addition of 37.5 ml of a lysozyme solution containing 0.5M of EDTA (pH 8.0) dissolved therein, after which it was stirred and alowed to stand on ice for 1 hour. The cells were sonicated in an ultrasonic manner and then subjected to centrifugation at 6,000 rpm for 5 minutes to collect the inclusion bodies. These inclusion bodies were solubilized with 6M of guanidine HCL, and adjustment was made so that the content of the solution was prepared. To the mixture were added 1 mM of oxidized glutathione and 10 mM of reduced glutathione, and then it was allowed to stand at pH 8.0 and room temperature for 10–16 hours. The mixture was dialyzed against a 50 mM glycine - sodium hydroxide buffer solution (pH 10.0) containing 5% glycerol, 100 mM of KCl and 0.05 mM of EDTA to yield the object polypeptides Fv(TU27) and Fv(TU25).

The behaviors of these substances in SDS polyacrylamide gel electrophoresis proved that their molecular weights are roughly in agreement with the values calculated for the amino acid sequences assumed according to Example 6. The determination of the amino acid sequences at the N-termini with a protein sequencer affirmed that they had sequences where methionine was attached to the N-termini of the anticipated amino acid sequences. Reference should be made to the Sequence Identification Nos. 1–4 in the sequence table.

Example 6

Determination of the Nucleotide Sequences and the Deduction of the Amino Acid Sequences The constructed plasmids pFv(TU27)-DE and pFv(TU25)-DE which express polypeptides consisting only of the V regions were purified according to the alkali SDS method, and their nucleotide sequences were determined with a 7-DEAZA sequence kit (produced by Takara Shuzo Inc.) using a commercially available sequencing primer M4 or RV (produced by Takara Shuzo Inc.). The amino acid sequences were assumed on the basis of the revealed nucleotide sequences.

Sequence Identification No. 1 in the sequence listing reflects the nucleotide sequence coding for polypeptide Fv(TU27) and the corresponding amino acid sequence, while Sequence Identification No.3 in the sequence listing shows the nucleotide sequence coding for polypeptide Fv(TU25) and the corresponding amino acid sequence. That is, as Sequence Identification No. 1 shows, polypeptide Fv(TU27) is a polypeptide consisting of 240 amino acids with Met at its N-terminal and Ser at its C-terminal (SEQ ID NO:2). In contrast, polypeptide Fv(TU25) is a polypeptide consisting of 239 amino acids with an N-terminal Met and an C-terminal Ser (SEQ ID NO:4).

The homology of the two sequences was calculated to be 94.2% for the L chains, whereas the value was 60.4% for the H chains. The total value was 76,8% for the L and H chains. This shows the existence of polypeptides, which are capable of binding to the β chain of human IL-2 receptor, regardless of a slight change in structure.

Example 7

Determination of the Antibody Activity of Polypeptides Fv(TU27) (SEQ ID NO:2) and Fv (TU25) (SEQ ID NO:4)

In an RPMI-1640 culture medium containing 0.5% BSA and 0.02% $NaN_2$ there were suspended $5\times10^5$ YT cells to which were added polypeptide Fv(TU27), TU27 antibody, polypeptide Fv(TU25) and TU25 antibody diluted with the same type culture medium to an appropriate concentration and then reacted for one hour at 4° C. Then a TU27 or TU25 antibody labelled with $^{125}I$ according to the chloramine T method was added to the mixture which was subjected to a 2 hour reaction at 4° C., after which the radioactivity bound to cell surfaces was measured. It was made clear that polypeptides Fv(TU27) and Fv(TU25) each have activity to inhibit the binding between TU27 monoclonal antibody (originating in hybridoma FERM BP-2510) or TU25 monoclonal antibody (originating in hybridoma FERM BP-3529) and the β chain of IL-2 receptor on the surface of each YT cell.

Next, in an RPMI-1640 culture medium containing 0.5% BSA and 0.02% $NaN_3$ there were suspended $5\times10^5$ MOLT4 cells with cDNA for the β chain of IL-2 receptor transfected therein. To the resulting suspension were added polypeptide Fv(TU27), TU27 monoclonal antibody (originating in hybridoma FERM BP-2510), polypeptide Fv(TU25) and TU25 monoclonal antibody (originating in hybridoma FERM BP-3529) diluted with the same type culture medium to an appropriate concentration, and this was reacted for one hour at 4° C. Then IL-2 labelled with $^{125}I$ according to the Bolton-Hunter method was added to the mixture which was subjected to a 2 hour reaction at 4° C., after which the radioactivity bound to the cell surfaces was measured. It became apparent that polypeptides Fv(TU27) and Fv(TU25) each have activity to inhibit the binding of IL-2 to a β chain of an IL-2 receptor.

EFFECTS OF THE INVENTION

Polypeptides according to the present invention consisting only of the V regions of an antibody which is capable of binding to the β chain of IL-2 receptor and of inhibiting the binding of IL-2 to the receptor may be utilized to provide a very safe immunosuppresive agent useful to prevent rejection of organ transplantation and to cure autoimmune diseases.

---

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 720 base pairs
        ( B ) TYPE: nucleic acid
        ( C ) STRANDEDNESS: unknown
        ( D ) TOPOLOGY: linear ( i i ) MOLECULE TYPE: DNA (genomic)

( i x ) FEATURE:
        ( A ) NAME/KEY: CDS
        ( B ) LOCATION: 1..720

( x i ) SEQUENCE DESCRIPTION: SEQ ID NO:1:

```
ATG  GAT  ATT  CTG  CTG  ACC  CAG  TCT  CCA  GCC  ATC  CTG  TCT  GTG  AGT  CCC        4 8
Met  Asp  Ile  Leu  Leu  Thr  Gln  Ser  Pro  Ala  Ile  Leu  Ser  Val  Ser  Pro
```

-continued

| | 1 | | | 5 | | | | | 10 | | | | | 15 | | |
|---|---|---|---|---|---|---|---|---|---|---|---|---|---|---|---|---|
| GGA | GAA | AGA | GTC | AGT | TTC | TCC | TGC | AGG | GCC | AGT | CAG | AGC | ATT | GGC | ACA | 96 |
| Gly | Glu | Arg | Val | Ser | Phe | Ser | Cys | Arg | Ala | Ser | Gln | Ser | Ile | Gly | Thr | |
| | | | 20 | | | | | 25 | | | | | 30 | | | |
| AGC | ATA | CAC | TGG | TAT | CAG | CAA | AGA | ACA | AAT | GGT | TCT | CCA | AGG | CTT | CTC | 144 |
| Ser | Ile | His | Trp | Tyr | Gln | Gln | Arg | Thr | Asn | Gly | Ser | Pro | Arg | Leu | Leu | |
| | | 35 | | | | | 40 | | | | | 45 | | | | |
| ATT | AAA | TAT | GCT | TCT | GAG | TCT | CTC | TCT | GGG | ATC | CCT | TCC | AGG | TTT | AGT | 192 |
| Ile | Lys | Tyr | Ala | Ser | Glu | Ser | Leu | Ser | Gly | Ile | Pro | Ser | Arg | Phe | Ser | |
| | 50 | | | | | 55 | | | | | 60 | | | | | |
| GGC | AGT | GGA | TCA | GGG | ACA | GAT | TTT | ACT | CTT | AGC | ATC | ACC | AGT | GTG | GAT | 240 |
| Gly | Ser | Gly | Ser | Gly | Thr | Asp | Phe | Thr | Leu | Ser | Ile | Thr | Ser | Val | Asp | |
| 65 | | | | | 70 | | | | | 75 | | | | | 80 | |
| TCT | GAA | GAT | ATT | GCA | GAT | TAT | TAC | TGT | CAA | CAA | ACT | AAT | AGC | TGG | CCA | 288 |
| Ser | Glu | Asp | Ile | Ala | Asp | Tyr | Tyr | Cys | Gln | Gln | Thr | Asn | Ser | Trp | Pro | |
| | | | | 85 | | | | | 90 | | | | | 95 | | |
| ACG | ACG | TTC | GGT | GGA | GGG | ACC | AAG | CTG | GAG | CTC | AAA | GTC | GAC | AAA | TCC | 336 |
| Thr | Thr | Phe | Gly | Gly | Gly | Thr | Lys | Leu | Glu | Leu | Lys | Val | Asp | Lys | Ser | |
| | | | 100 | | | | | 105 | | | | | 110 | | | |
| TCA | GGA | TCT | GGC | TCC | GAA | TCC | AAA | AGC | ACC | CAG | GTC | AAA | CTC | GAG | GAG | 384 |
| Ser | Gly | Ser | Gly | Ser | Glu | Ser | Lys | Ser | Thr | Gln | Val | Lys | Leu | Glu | Glu | |
| | | 115 | | | | | 120 | | | | | 125 | | | | |
| TCT | GGA | CCT | GGC | CTG | GTG | AAA | CCT | TCT | CAG | TCT | CTG | TCC | CTC | ACC | TGC | 432 |
| Ser | Gly | Pro | Gly | Leu | Val | Lys | Pro | Ser | Gln | Ser | Leu | Ser | Leu | Thr | Cys | |
| | 130 | | | | | 135 | | | | | 140 | | | | | |
| ACT | GTC | ACT | GGC | TAC | CCA | ATC | ACC | AGT | GAT | TAT | GCC | TGG | GAC | TGG | ATC | 480 |
| Thr | Val | Thr | Gly | Tyr | Pro | Ile | Thr | Ser | Asp | Tyr | Ala | Trp | Asp | Trp | Ile | |
| 145 | | | | | 150 | | | | | 155 | | | | | 160 | |
| CGG | CAG | TTT | CCA | GGA | AAC | AAA | CTG | GAG | TGG | ATG | GGC | TAC | GTA | AGC | TAC | 528 |
| Arg | Gln | Phe | Pro | Gly | Asn | Lys | Leu | Glu | Trp | Met | Gly | Tyr | Val | Ser | Tyr | |
| | | | | 165 | | | | | 170 | | | | | 175 | | |
| AGT | GGT | AGC | ACT | GAC | TAC | AAC | CCA | TCT | CTC | AAA | AGT | CGA | ATC | TCT | ATC | 576 |
| Ser | Gly | Ser | Thr | Asp | Tyr | Asn | Pro | Ser | Leu | Lys | Ser | Arg | Ile | Ser | Ile | |
| | | | 180 | | | | | 185 | | | | | 190 | | | |
| AGT | CGA | GAC | ACA | TCC | AAG | AAC | CAG | TTC | TTC | CTG | CAG | TTG | AAT | TCT | GTC | 624 |
| Ser | Arg | Asp | Thr | Ser | Lys | Asn | Gln | Phe | Phe | Leu | Gln | Leu | Asn | Ser | Val | |
| | | 195 | | | | | 200 | | | | | 205 | | | | |
| ACT | ACT | GAG | GAC | ACA | GCC | ACA | TAT | TAC | TGT | GCA | AGA | GGT | GGT | TTC | CCC | 672 |
| Thr | Thr | Glu | Asp | Thr | Ala | Thr | Tyr | Tyr | Cys | Ala | Arg | Gly | Gly | Phe | Pro | |
| | 210 | | | | | 215 | | | | | 220 | | | | | |
| TAT | GCT | ATG | GAC | TAC | TGG | GGT | CAA | GGG | ACC | ACG | GTC | ACC | GTC | TCC | TCA | 720 |
| Tyr | Ala | Met | Asp | Tyr | Trp | Gly | Gln | Gly | Thr | Thr | Val | Thr | Val | Ser | Ser | |
| 225 | | | | | 230 | | | | | 235 | | | | | 240 | |

( 2 ) INFORMATION FOR SEQ ID NO:2:

( i ) SEQUENCE CHARACTERISTICS:
        ( A ) LENGTH: 240 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Asp | Ile | Leu | Leu | Thr | Gln | Ser | Pro | Ala | Ile | Leu | Ser | Val | Ser | Pro |
|---|---|---|---|---|---|---|---|---|---|---|---|---|---|---|---|
| 1 | | | | 5 | | | | | 10 | | | | | 15 | |

| Gly | Glu | Arg | Val | Ser | Phe | Ser | Cys | Arg | Ala | Ser | Gln | Ser | Ile | Gly | Thr |
|---|---|---|---|---|---|---|---|---|---|---|---|---|---|---|---|
| | | | 20 | | | | | 25 | | | | | 30 | | |

| Ser | Ile | His | Trp | Tyr | Gln | Gln | Arg | Thr | Asn | Gly | Ser | Pro | Arg | Leu | Leu |
|---|---|---|---|---|---|---|---|---|---|---|---|---|---|---|---|
| | | 35 | | | | | 40 | | | | | 45 | | | |

| Ile | Lys | Tyr | Ala | Ser | Glu | Ser | Leu | Ser | Gly | Ile | Pro | Ser | Arg | Phe | Ser |
|---|---|---|---|---|---|---|---|---|---|---|---|---|---|---|---|

|        |       |       |       |       |       |       |       |       |       |       |       |       |       |       |       |
|--------|-------|-------|-------|-------|-------|-------|-------|-------|-------|-------|-------|-------|-------|-------|-------|
|        |       |       |       | 50    |       |       |       | 55    |       |       |       | 60    |       |       |       |
| Gly<br>65 | Ser | Gly | Ser | Gly | Thr<br>70 | Asp | Phe | Thr | Leu | Ser<br>75 | Ile | Thr | Ser | Val | Asp<br>80 |
| Ser | Glu | Asp | Ile | Ala<br>85 | Asp | Tyr | Tyr | Cys | Gln<br>90 | Gln | Thr | Asn | Ser | Trp<br>95 | Pro |
| Thr | Thr | Phe | Gly<br>100 | Gly | Gly | Thr | Lys | Leu<br>105 | Glu | Leu | Lys | Val | Asp<br>110 | Lys | Ser |
| Ser | Gly | Ser<br>115 | Gly | Ser | Glu | Ser | Lys<br>120 | Ser | Thr | Gln | Val | Lys<br>125 | Leu | Glu | Glu |
| Ser | Gly<br>130 | Pro | Gly | Leu | Val | Lys<br>135 | Pro | Ser | Gln | Ser | Leu<br>140 | Ser | Leu | Thr | Cys |
| Thr<br>145 | Val | Thr | Gly | Tyr | Pro<br>150 | Ile | Thr | Ser | Asp | Tyr<br>155 | Ala | Trp | Asp | Trp | Ile<br>160 |
| Arg | Gln | Phe | Pro | Gly<br>165 | Asn | Lys | Leu | Glu | Trp<br>170 | Met | Gly | Tyr | Val | Ser<br>175 | Tyr |
| Ser | Gly | Ser | Thr<br>180 | Asp | Tyr | Asn | Pro | Ser<br>185 | Leu | Lys | Ser | Arg | Ile<br>190 | Ser | Ile |
| Ser | Arg | Asp<br>195 | Thr | Ser | Lys | Asn | Gln<br>200 | Phe | Phe | Leu | Gln | Leu<br>205 | Asn | Ser | Val |
| Thr<br>210 | Thr | Glu | Asp | Thr | Ala<br>215 | Thr | Tyr | Tyr | Cys | Ala<br>220 | Arg | Gly | Gly | Phe | Pro |
| Tyr<br>225 | Ala | Met | Asp | Tyr | Trp<br>230 | Gly | Gln | Gly | Thr | Thr<br>235 | Val | Thr | Val | Ser | Ser<br>240 |

( 2 ) INFORMATION FOR SEQ ID NO:3:

( i ) SEQUENCE CHARACTERISTICS:
        ( A ) LENGTH: 717 base pairs
        ( B ) TYPE: nucleic acid
        ( C ) STRANDEDNESS: unknown
        ( D ) TOPOLOGY: linear ( i i ) MOLECULE TYPE: DNA (genomic)

( i x ) FEATURE:
        ( A ) NAME/KEY: CDS
        ( B ) LOCATION: 1..717

( x i ) SEQUENCE DESCRIPTION: SEQ ID NO:3:

| ATG | GAC | ATT | CAG | CTG | ACC | CAG | TCT | CCA | GCC | ATC | CTG | TCT | GTG | AGT | CCA | 48 |
|-----|-----|-----|-----|-----|-----|-----|-----|-----|-----|-----|-----|-----|-----|-----|-----|----|
| Met<br>1 | Asp | Ile | Gln | Leu<br>5 | Thr | Gln | Ser | Pro | Ala<br>10 | Ile | Leu | Ser | Val | Ser<br>15 | Pro | |
| GGA | GAA | AGA | GTC | AGT | TTC | TCC | TGC | AGG | GCC | AGT | CAG | ACC | ATT | GGG | ACA | 96 |
| Gly | Glu | Arg | Val<br>20 | Ser | Phe | Ser | Cys | Arg<br>25 | Ala | Ser | Gln | Thr | Ile<br>30 | Gly | Thr | |
| AGC | ATA | CAC | TGG | TAT | CAG | CAA | AGA | ACA | AAT | GGT | TCT | CCA | AGG | CTT | CTC | 144 |
| Ser | Ile | His<br>35 | Trp | Tyr | Gln | Gln | Arg<br>40 | Thr | Asn | Gly | Ser | Pro<br>45 | Arg | Leu | Leu | |
| ATA | AAG | TAT | GCT | TCT | GAG | TCT | ATC | TCT | GGG | ATC | CCT | TCC | AGG | TTT | AGT | 192 |
| Ile | Lys<br>50 | Tyr | Ala | Ser | Glu | Ser<br>55 | Ile | Ser | Gly | Ile | Pro<br>60 | Ser | Arg | Phe | Ser | |
| GGG | AGT | GGA | TCA | GGG | ACA | GAT | TTT | ACT | CTT | AGC | ATC | AAC | AAT | GTG | GAG | 240 |
| Gly<br>65 | Ser | Gly | Ser | Gly | Thr<br>70 | Asp | Phe | Thr | Leu | Ser<br>75 | Ile | Asn | Asn | Val | Glu<br>80 | |
| TCT | GAA | GAT | ATT | GCA | GAT | TAT | TAC | TGT | CAA | CAA | ACT | AAT | ACC | TGG | CCA | 288 |
| Ser | Glu | Asp | Ile | Ala<br>85 | Asp | Tyr | Tyr | Cys | Gln<br>90 | Gln | Thr | Asn | Thr | Trp<br>95 | Pro | |
| ACG | ACG | TTC | GGC | TCG | GGG | ACC | AAG | CTG | GAG | CTC | AAA | GTC | GAC | AAA | TCC | 336 |
| Thr | Thr | Phe | Gly<br>100 | Ser | Gly | Thr | Lys | Leu<br>105 | Glu | Leu | Lys | Val | Asp<br>110 | Lys | Ser | |

| | | | | | | | | | | | | | | | | |
|---|---|---|---|---|---|---|---|---|---|---|---|---|---|---|---|---|
| TCA | GGA | TCT | GGC | TCC | GAA | TCC | AAA | AGC | ACG | CAG | GTC | AAA | CTC | GAG | CAG | 384 |
| Ser | Gly | Ser | Gly | Ser | Glu | Ser | Lys | Ser | Thr | Gln | Val | Lys | Leu | Glu | Gln | |
| | | 115 | | | | | 120 | | | | | 125 | | | | |
| TCA | GGG | GGA | GGC | TTA | GTG | AAG | CCT | GGA | GGG | TCC | CTG | AAA | CTC | TCC | TGT | 432 |
| Ser | Gly | Gly | Gly | Leu | Val | Lys | Pro | Gly | Gly | Ser | Leu | Lys | Leu | Ser | Cys | |
| | 130 | | | | | 135 | | | | | | 140 | | | | |
| GCA | GCC | TCT | GGA | TTC | GCT | TTC | AGT | AGT | TAT | GAC | ATG | TCT | TGG | GTT | CGC | 480 |
| Ala | Ala | Ser | Gly | Phe | Ala | Phe | Ser | Ser | Tyr | Asp | Met | Ser | Trp | Val | Arg | |
| 145 | | | | | 150 | | | | | 155 | | | | | 160 | |
| CAG | ACT | CCG | GAG | AAG | AGG | CTG | AAC | TGG | GTC | GCA | ACC | TTT | AGT | AGT | GAT | 528 |
| Gln | Thr | Pro | Glu | Lys | Arg | Leu | Asn | Trp | Val | Ala | Thr | Phe | Ser | Ser | Asp | |
| | | | | 165 | | | | | 170 | | | | | 175 | | |
| GGT | AGT | GAC | ACC | GAC | TAT | CCA | GAC | AGT | GTG | AAG | GGC | CGA | TTC | ACC | ATC | 576 |
| Gly | Ser | Asp | Thr | Asp | Tyr | Pro | Asp | Ser | Val | Lys | Gly | Arg | Phe | Thr | Ile | |
| | | | 180 | | | | | 185 | | | | | 190 | | | |
| TCC | AGA | GAC | AAT | GCC | AGG | AAC | ACC | CTG | TAC | CTG | CAA | ATG | AGC | AGT | CTG | 624 |
| Ser | Arg | Asp | Asn | Ala | Arg | Asn | Thr | Leu | Tyr | Leu | Gln | Met | Ser | Ser | Leu | |
| | | 195 | | | | | 200 | | | | | 205 | | | | |
| AGG | TCT | GAG | GAC | ACG | GCC | TTG | TAT | TAC | TGT | GCA | AGG | GGG | TAC | CCC | TAT | 672 |
| Arg | Ser | Glu | Asp | Thr | Ala | Leu | Tyr | Tyr | Cys | Ala | Arg | Gly | Tyr | Pro | Tyr | |
| | 210 | | | | | 215 | | | | | 220 | | | | | |
| GCT | ATG | GAC | TAC | TGG | GGT | CAA | GGG | ACC | ACG | GTC | ACC | GTC | TCC | TCA | | 717 |
| Ala | Met | Asp | Tyr | Trp | Gly | Gln | Gly | Thr | Thr | Val | Thr | Val | Ser | Ser | | |
| 225 | | | | | 230 | | | | | 235 | | | | | | |

( 2 ) INFORMATION FOR SEQ ID NO:4:

( i ) SEQUENCE CHARACTERISTICS:
        ( A ) LENGTH: 239 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Asp | Ile | Gln | Leu | Thr | Gln | Ser | Pro | Ala | Ile | Leu | Ser | Val | Ser | Pro |
| 1 | | | | 5 | | | | | 10 | | | | | 15 | |
| Gly | Glu | Arg | Val | Ser | Phe | Ser | Cys | Arg | Ala | Ser | Gln | Thr | Ile | Gly | Thr |
| | | | 20 | | | | | 25 | | | | | 30 | | |
| Ser | Ile | His | Trp | Tyr | Gln | Gln | Arg | Thr | Asn | Gly | Ser | Pro | Arg | Leu | Leu |
| | | | 35 | | | | | 40 | | | | | 45 | | |
| Ile | Lys | Tyr | Ala | Ser | Glu | Ser | Ile | Ser | Gly | Ile | Pro | Ser | Arg | Phe | Ser |
| | | 50 | | | | | 55 | | | | | 60 | | | |
| Gly | Ser | Gly | Ser | Gly | Thr | Asp | Phe | Thr | Leu | Ser | Ile | Asn | Asn | Val | Glu |
| 65 | | | | | 70 | | | | | 75 | | | | | 80 |
| Ser | Glu | Asp | Ile | Ala | Asp | Tyr | Tyr | Cys | Gln | Gln | Thr | Asn | Thr | Trp | Pro |
| | | | | 85 | | | | | 90 | | | | | 95 | |
| Thr | Thr | Phe | Gly | Ser | Gly | Thr | Lys | Leu | Glu | Leu | Lys | Val | Asp | Lys | Ser |
| | | | 100 | | | | | 105 | | | | | 110 | | |
| Ser | Gly | Ser | Gly | Ser | Glu | Ser | Lys | Ser | Thr | Gln | Val | Lys | Leu | Glu | Gln |
| | | | 115 | | | | | 120 | | | | | 125 | | |
| Ser | Gly | Gly | Gly | Leu | Val | Lys | Pro | Gly | Gly | Ser | Leu | Lys | Leu | Ser | Cys |
| | 130 | | | | | 135 | | | | | | 140 | | | |
| Ala | Ala | Ser | Gly | Phe | Ala | Phe | Ser | Ser | Tyr | Asp | Met | Ser | Trp | Val | Arg |
| 145 | | | | | 150 | | | | | 155 | | | | | 160 |
| Gln | Thr | Pro | Glu | Lys | Arg | Leu | Asn | Trp | Val | Ala | Thr | Phe | Ser | Ser | Asp |
| | | | | 165 | | | | | 170 | | | | | 175 | |
| Gly | Ser | Asp | Thr | Asp | Tyr | Pro | Asp | Ser | Val | Lys | Gly | Arg | Phe | Thr | Ile |
| | | | 180 | | | | | 185 | | | | | 190 | | |

| | | | | | | | | | | | | | | |
|---|---|---|---|---|---|---|---|---|---|---|---|---|---|---|
| Ser | Arg | Asp<br>195 | Asn | Ala | Arg | Asn | Thr<br>200 | Leu | Tyr | Leu | Gln | Met<br>205 | Ser | Ser | Leu |
| Arg | Ser<br>210 | Glu | Asp | Thr | Ala | Leu<br>215 | Tyr | Tyr | Cys | Ala | Arg<br>220 | Gly | Tyr | Pro | Tyr |
| Ala<br>225 | Met | Asp | Tyr | Trp | Gly<br>230 | Gln | Gly | Thr | Thr | Val<br>235 | Thr | Val | Ser | Ser | |

We claim:

1. An immunosuppressive composition comprising:
   an effective amount of polypeptide selected from the group consisting of SEQ ID NO:2 and SEQ ID NO:4.

2. A polypeptide selected from the group consisting of:
   a) polypeptide SEQ ID NO:2, and
   b) a polypeptide which in respect to (a) lacks the N-terminal Met residue.

3. A polypeptide selected from the group consisting of:
   a) polypeptide SEQ ID NO:4, and
   b) a polypeptide, which in respect to (a) lacks the N-terminal Met residue.

4. A DNA sequence coding for
   a) polypeptide SEQ ID NO:2, or
   b) a polypeptide, which in respect to (a) lacks the N-terminal Met residue.

5. A DNA selected from the group consisting of SEQ ID NO:1 and SEQ ID NO:3.

6. DNA of SEQ ID NO:3.

7. An expression vector comprising a DNA selected from the group consisting of SEQ ID NO:1 and SEQ ID NO:3.

8. A transformant comprising a vector containing a DNA selected from the group consisting of SEQ ID NO:1 and SEQ ID NO:3.

9. The transformant of claim 8, which is a eukaryotic cell.

10. The transformant of claim 8, which is a prokaryotic cell.

11. The transformant of claim 8, which belongs to the genus Escherichia.

12. The transformant of claim 8, which is FERM BP-3973 or FERM BP-3974.

13. The transformant of claim 11, which belongs to *E. coli*.

14. A process for producing a polypeptide comprising:
    cultivating a transformant containing an expression vector capable of expressing a peptide selected from the group consisting of SEQ ID NO:2 and SEQ ID NO:4.

* * * * *